United States Patent
Thrush et al.

(10) Patent No.: US 10,186,539 B2
(45) Date of Patent: Jan. 22, 2019

(54) HEATED IMAGE SENSOR WINDOW

(71) Applicant: BIO-RAD LABORATORIES, INC., Hercules, CA (US)

(72) Inventors: Evan Thrush, San Anselmo, CA (US); Steve Swihart, Walnut Creek, CA (US); Hari Jayamohan, Salt Lake City, UT (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/875,898

(22) Filed: Oct. 6, 2015

(65) Prior Publication Data
US 2016/0104806 A1 Apr. 14, 2016

Related U.S. Application Data

(60) Provisional application No. 62/063,060, filed on Oct. 13, 2014.

(51) Int. Cl.
*H04N 1/00* (2006.01)
*H01L 27/146* (2006.01)
(Continued)

(52) U.S. Cl.
CPC ......... *H01L 27/1462* (2013.01); *G01N 21/15* (2013.01); *H01L 23/34* (2013.01);
(Continued)

(58) Field of Classification Search
None
See application file for complete search history.

(56) References Cited

U.S. PATENT DOCUMENTS 4,926,227 A * 5/1990 Jensen ............... H01L 23/38
257/215
5,485,005 A * 1/1996 Aikens ............... H01J 31/49
250/214 VT
(Continued)

FOREIGN PATENT DOCUMENTS

GB 2414559 B 8/2007

OTHER PUBLICATIONS

Author: Lee et al. Title: "Zwitter-Wettability and Antifogging Coatings with Frost-Resisting Capabilities" Date: Jan. 29, 2013.*
(Continued)

*Primary Examiner* — Twyler L Haskins
*Assistant Examiner* — Wesley J Chiu
(74) *Attorney, Agent, or Firm* — Kilpatrick Townsend and Stockton LLP

(57) ABSTRACT

An image sensor assembly having a sensor window positioned in front of an image sensor, having structure and/or characteristics to prevent the formation of condensation on the sensor window. Structure to prevent the formation of condensation includes thin films which can have anti-condensation, anti-reflective, electrically conductive, and/or thermally conductive properties. The sensor window can further have a textured surface to displace water so as to avoid condensation formation on the window surface. The sensor window, and in some embodiments a frame, can be maintained at an elevated temperature proximate to the image sensor during operation to prevent the formation of condensation.

17 Claims, 10 Drawing Sheets

(51) Int. Cl.
*H01L 23/34* (2006.01)
*H01L 31/024* (2014.01)
*G01N 21/15* (2006.01)
*G01N 21/64* (2006.01)
*G01N 21/76* (2006.01)

(52) U.S. Cl.
CPC ...... H01L 27/14618 (2013.01); H01L 31/024 (2013.01); H04N 1/00986 (2013.01); *G01N 21/6456* (2013.01); *G01N 21/76* (2013.01); *G01N 21/763* (2013.01); *G01N 2021/158* (2013.01)

(56) References Cited

U.S. PATENT DOCUMENTS

| | | | | |
|---|---|---|---|---|
| 5,508,740 | A * | 4/1996 | Miyaguchi | H01L 23/34 257/E23.08 |
| 5,856,866 | A | 1/1999 | Shimizu et al. | |
| 6,072,232 | A | 6/2000 | Li et al. | |
| 7,211,771 | B1 * | 5/2007 | Smith | E01F 9/40 116/202 |
| 2005/0141106 | A1 | 6/2005 | Lee et al. | |
| 2005/0206780 | A1 * | 9/2005 | Iwasaki | B60R 1/00 348/373 |
| 2007/0109441 | A1 * | 5/2007 | Cheng | G08B 13/19619 348/373 |
| 2007/0152065 | A1 | 7/2007 | Gong et al. | |
| 2009/0046183 | A1 * | 2/2009 | Nishida | H01L 21/6835 348/294 |
| 2009/0122178 | A1 * | 5/2009 | Kwon | H01L 27/14618 348/340 |
| 2010/0214430 | A1 * | 8/2010 | De Boer | G01N 21/6458 348/222.1 |
| 2012/0080214 | A1 * | 4/2012 | Weaver | H01L 23/3677 174/110 R |
| 2012/0134025 | A1 | 5/2012 | Hart | |
| 2012/0182469 | A1 * | 7/2012 | Shintani | H04N 5/2254 348/374 |
| 2012/0249865 | A1 * | 10/2012 | Ichikawa | H04N 5/2252 348/373 |
| 2013/0141626 | A1 * | 6/2013 | Hasegawa | H01L 27/14618 348/340 |
| 2013/0249375 | A1 * | 9/2013 | Panagotacos | H05B 33/0803 313/13 |
| 2014/0036064 | A1 * | 2/2014 | Lu | B60Q 9/005 348/118 |
| 2015/0253250 | A1 * | 9/2015 | Noda | G01N 21/76 435/288.7 |
| 2016/0222227 | A1 * | 8/2016 | Han | C09D 5/24 |
| 2016/0313827 | A1 * | 10/2016 | Song | G06F 3/044 |

OTHER PUBLICATIONS

Title: "Thermal Conductivity of some common Materials" Date: Feb. 16, 2006 URL: https://web.archive.org/web/20060216234044/http://www.engineeringtoolbox.com/thermal-conductivity-d_429.html.*
Title: Soda-lime glass Date: Mar. 3, 2009 URL: https://web.archive.org/web/20090303155402/https://en.wikipedia.org/wiki/Soda-lime_glass.*
Title: "Borosilicate Glass—Properties of Borosilicate Glass (Pyrex_Duran) by Goodfellow Ceramic & Glass Division" Address: https://www.azom.com/article.aspx?ArticleID=4765 Date: Jun. 15, 2009.*
International Search Report and Written Opinion dated Feb. 12, 2016 in PCT/US15/54185, 13 pages.
First Chinese Office Action in CN Application 201580055397.7 dated Apr. 3, 2018 (and English translation); 17 pages.
Extended European Search Report in EP Application 15850115.5 dated Apr. 24, 2018; 17 pages.
Anonymous; "TIE-31: Mechanical and thermal properties of optical glass"; retrieved from the Internet at http://www.schott.com/d/advanced opfics/d08c2fb9-c2f2-4861-a57b-18495ef5a4fb/1.2/schott_tie-31_mechanical_and_thermal_propertes_of_optical_eng.pdf; Jul. 2004; Schott AG; 10 pages.

* cited by examiner

HEATED IMAGE SENSOR WINDOW

CROSS-REFERENCE TO RELATED APPLICATIONS

The present application claims the benefit of priority to U.S. provisional application No. 62/063,060, entitled "HEATED IMAGE SENSOR WINDOW", filed on Oct. 13, 2014, which is hereby incorporated by reference.

FIELD OF THE INVENTION

The present invention generally relates to the field of imaging and apparatus for imaging biological and chemical test and assay results. More specifically, many embodiments are directed to an imaging apparatus for viewing electrophoresis gels, nucleic acid blots, protein blots, Western blots, or similar biochemical tests and assays using chemiluminescent, fluorescent, or phosphorescent markers.

BACKGROUND OF THE INVENTION

Instruments and apparatus systems that are used for viewing, recording, and analyzing the results of biological and chemical tests and assays often require instrumentation such as a charge-coupled device (CCD) camera, a complementary metal-oxide-semiconductor (CMOS) imager, or other such image sensor. Such instrumentation can further incorporate CCD or CMOS cameras into microscopes and the like. In such instrumentation, the surface of a CCD or CMOS camera widow, or other glass or transparent surface, can be subject to environmental humidity, moisture, or fogging condensing on the surface, in the optical path of the camera or imaging sensor. Such condensation that reaches the window of a CCD or CMOS camera or other such image capturing sensor of imaging instrumentation can reduce the quality and accuracy of an imaged sample.

SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments and aspects of the invention in a simplified form as a prelude to the more detailed description that is presented later.

One embodiment of the present disclosure is generally directed toward an image sensor assembly which can include a cooling structure, such as a thermoelectric cooling element (TEC), an image sensor, where the image sensor can be positioned along an optical path that is set to view a sample region, the image sensor further being coupled to, and cooled by the TEC; and a sensor window arranged between the image sensor and the sample region. In some aspects, the image sensor assembly sensor window can be coated with an anti-fog coating on an exterior surface of the sensor window. In many aspects, the image sensor assembly is configured to image electrophoresis gels, nucleic acids blots, protein blots, bioluminescent assay results, and/or chemiluminescent assay results. In further aspects, the image sensor assembly can be heated with a heat source, which in some aspects can be heat generated by a TEC. In some aspects, the sensor window of the image sensor assembly can have a thermal conductivity ($\kappa$) of about 0.04-1.14 W/(m*K). In other aspects, the sensor window of the image sensor assembly can have a linear coefficient of thermal expansion ($\alpha_L$) of about $3\times10^{-6}$-$80\times10^{-6}$(1/K).

Another embodiment of the present disclosure is generally directed toward an image sensor assembly which can include a cooling structure, such as a thermoelectric cooling element (TEC); an image sensor, where the image sensor can be positioned along an optical path to view a sample region, the image sensor further being coupled to and cooled by a TEC; and a heating frame arranged at a position encircling at least a portion of the optical path between the image sensor and the sample region, the heating frame conducting heat generated by a TEC to form a region of space with heated air between the image sensor and the sample region. In some aspects, the heating frame of the image sensor assembly can be suspended by frame struts at a position about five millimeters (5 mm) from the image sensor. In many aspects, image sensor assembly is configured to image electrophoresis gels, nucleic acids blots, protein blots, bioluminescent assay results, and/or chemiluminescent assay results. In further aspects, the heating frame of the image sensor assembly can be heated with heat generated by a TEC.

A further embodiment of the present disclosure is generally directed toward an image sensor assembly which can include a cooling structure, such as a thermoelectric cooling element (TEC); an image sensor, where the image sensor can be positioned along an optical path to view a sample region, the image sensor further being coupled to and cooled by a TEC; and a concave sensor window arranged between the image sensor and the sample region, the concave surface of the concave sensor window facing the image sensor, with a cavity formed between the concave surface of the concave sensor window. In some aspects, the concave sensor window can be heated with heat generated by a TEC. In other aspects, the concave sensor window can be coated with an anti-fog coating on an exterior surface of the concave sensor window. In further aspects, the concave sensor window can have a rough or zwitter-textured surface. In many aspects, the image sensor assembly can be configured to image electrophoresis gels, nucleic acids blots, protein blots, bioluminescent assay results, and/or chemiluminescent assay results. In some aspects, the concave sensor window of the image sensor assembly can be a curved concave sensor window. In other aspects, the concave sensor window of the image sensor assembly can be a bulged concave sensor window. In further aspects, the concave sensor window of the image sensor assembly can be a doubled concave sensor window. In some aspects, the concave sensor window of the image sensor assembly, the concave sensor window can have a thermal conductivity ($\kappa$) of about 0.04-1.14 W/(m*K). In other aspects, the concave sensor window of the image sensor assembly can have a linear coefficient of thermal expansion ($\alpha_L$) of about $3\times10^{-6}$-$80\times10^{-6}$(1/K).

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

Illustrative aspects and embodiments are described in detail below with reference to the following drawing figures.

DETAILED DESCRIPTION OF THE INVENTION

Figure 1:
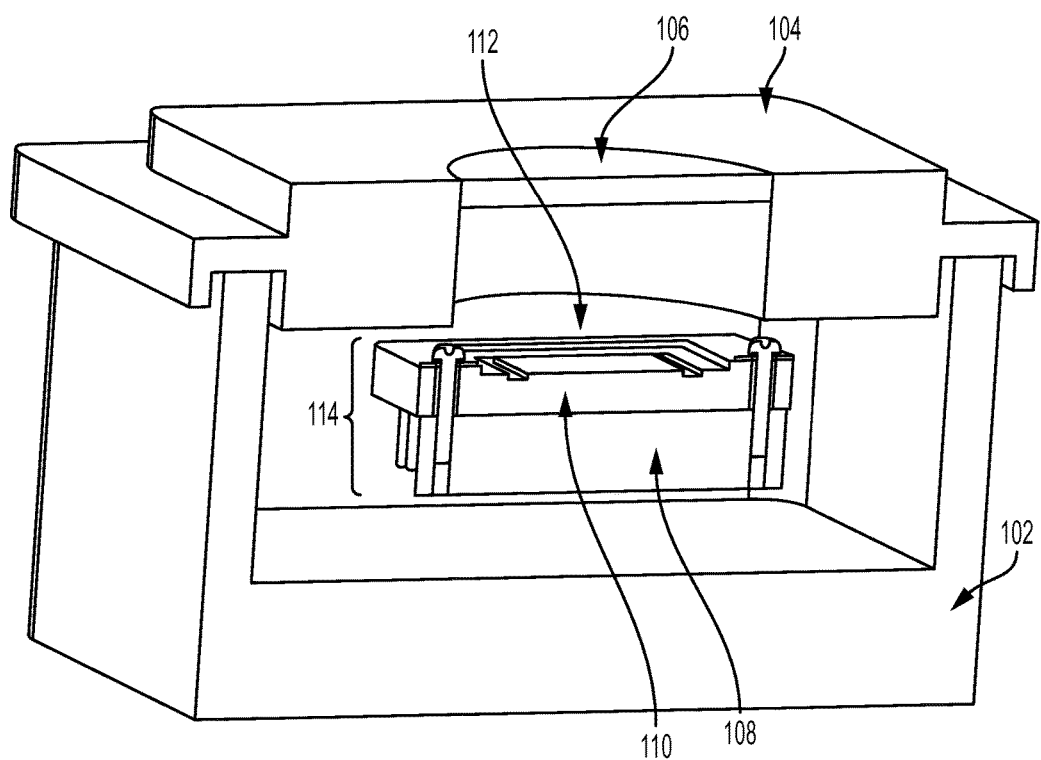
FIG. 1 is a cross-sectional perspective schematic representing elements of an imaging system chamber for an image sensor system.

Throughout this description for the purposes of explanation, numerous specific details are set forth in order to provide a thorough understanding of the many embodiments disclosed herein. It will be apparent, however, to one skilled in the art that the many embodiments may be practiced without some of these specific details. In other instances, well-known structures and devices are shown in diagram or schematic form to avoid obscuring the underlying principles of the described embodiments.

Imaging systems, apparatus, and instrumentation for imaging results from various biological, chemical, and/or biochemical tests and assays often use the light emitted by chemiluminescent, fluorescent, or phosphorescent markers in samples to form an images and identify characteristics of a sample. Such light can be captured by image sensors, which can be further contained within sealed structures that maintain an environment generally free of dust or other particulate matter to ensure a clear and accurate image of samples viewed by the imaging system. In some apparatus, however, humidity and condensation cannot be completely excluded from the imaging chamber. Condensation can thus form on transparent surfaces or sensory elements, which can be made of materials such as glass or polymer surfaces, located on or within the optical path of an image sensor. Such condensation can obscure and diminish the precision of images acquired with the image sensor by the imaging system.

There is considerable cost and complexity involved in building, evacuating, and sealing the imaging chamber for the purpose of preventing condensation from depositing on transparent surfaces like an image sensor. There is further cost and complexity in maintaining a constant temperature of the imaging chamber environment to manage and minimize condensation within the imaging chamber. The complexity of such systems is reflected when the imaging chamber is further evacuated and filled with a dry and/or inert gas, or optionally with a physical desiccant also in the chamber, to attempt to minimize any condensation inside the chamber.

In many imaging systems, however, a cooled camera system often includes a CCD or CMOS coupled on or to a thermoelectric cooler (TEC) with a heat exchange mechanism. The thermal energy drawn or generated by the TEC can be repurposed to heat other elements of the image sensor assembly. Thus, in some embodiments of the present disclosure, heat pumped out by the TEC is conducted to a sensor window positioned over or across an image sensor, which can thereby prevent the sensor window connected to the image sensor and CCD or CMOS from becoming cooler than the ambient environment, resulting in condensation forming on the sensor window. In further embodiments, the sensor window can be a convex window, forming a pocket of air or gas which can function as an insulating space or cavity between the image sensor and the sensor window. In other embodiments of the present disclosure, heat pumped out by the TEC is conducted to a heating frame proximate or adjacent to an image sensor, generating a region of elevated temperature which can thereby prevent condensation from forming on the image sensor. In alternative embodiments, a cooling system or cooling structure for the imaging system could be a fan, a refrigeration unit, a liquid heat exchanger, or the like.

As used herein, unless otherwise indicated, relative positional terms including, but not limited to, "before", "after", "in front of", "behind", "between", and the like refer to the positioning of elements relative to the optical path of light incident on or transmitting through such elements. As discussed herein, such elements positioned relative to each other are optical structures, can include windows, image sensors, framing elements, lenses, filters, absorbance glass, light sensors, and the like.

FIG. 1 is a cross-sectional schematic representing elements of an imaging system chamber for an image sensor system 100, as known in the art. An approach to reduce the amount of condensation within an imaging system is to construct a sealed casing, effectively isolating or sealing the environment in which the imaging sensor is housed to minimize the amount of gaseous water in close proximity to the imaging sensor and any transparent surfaces applied in the optical path of the imaging sensor. As shown, a chamber body 102 and a chamber front 104 can be mechanically coupled together to form a sealed interior environment, defined to be the imaging chamber 114. The chamber front 104 can be constructed or fabricated to have a location for a chamber window 106 through which an image sensor 110 receives light from a sample, defining an optical path from a sample to the image sensor. The image sensor 110 is mounted in a casing that includes a sensor window 112, which is also in line with the optical path from a sample to the image sensor 110. The image sensor 110 casing is connected, at the back of the image sensor 110, to a thermoelectric cooler (TEC) 108 that cools a CCD camera to an operational temperature. The image sensor 110 is sealed within the imaging chamber 114, where the imaging chamber can further be evacuated and filled with an inert gas and/or noble gas, such as argon, during manufacturing. In some aspects, the imaging chamber 114 can have a physical desiccant, such as a desiccant packet or pouch, placed inside the imaging chamber 114 to absorb any moisture that may leak or enter into the imaging chamber 114 during manufacture, or during service if the imaging chamber 114 seal requires breaking.

In such image sensor systems 100, a window front facing the lens of an image sensor 110 should remain at or above ambient temperature to prevent condensation from collecting or forming, which would interfere with imaging. The inert gas and desiccant inside the imaging chamber 114 can function to minimize moisture from being present in significant concentration or quantities inside the imaging chamber 114, and thereby prevent condensation from forming on a sensor window or other surface. Such systems, however, require the use of a sealed imaging chamber 114.

As described in aspects and embodiments of the present disclosure, thin film dielectric layers filters can be both optically transparent in relevant light wavelength ranges and electrically conductive. When applied to a glass or polymer substrate (such as a sensor window), a thin film dielectric layer can be electrically connected to a power source, thereby emitting a degree of thermal energy as part of an active or passive circuit, and thus preventing moisture from condensing on the thin film. Similarly, when applied to or mounted on a frame, a thin film dielectric layer electrically connected to a power source and configured to emit a degree of thermal energy as part of an active or passive circuit can thus prevent moisture from condensing on structural elements proximate or adjacent to the thin film.

While the many embodiments and aspects disclosed herein are generally directed to a heated or anti-condensation element for an imaging sensor and imaging system, the heated or anti-condensation imaging apparatus described herein can be used for any application where condensation may obscure or cloud an imaging sensor in a controlled or open environment, where prevention of condensation would be appropriate or advantageous.

Figure 2:
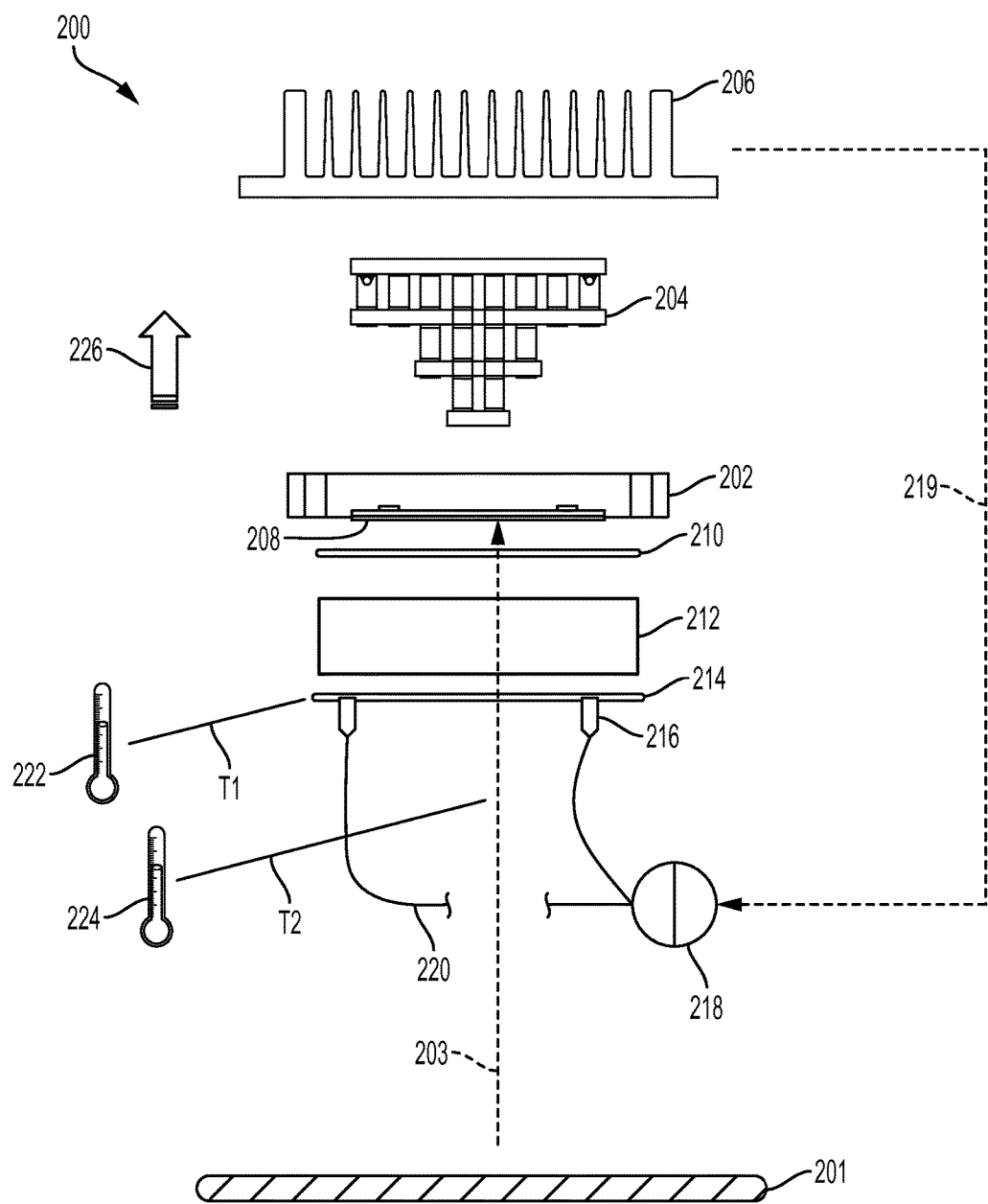
FIG. 2 is a schematic representing an exploded cross-sectional view of a configuration of elements for a heated image sensor system having a sensor window, according to some aspects or embodiments.

FIG. 2 is a schematic representing an exploded cross-sectional view of a configuration of elements for a heated image sensor system having a sensor window 200. The image sensor 202 can be positioned in relation to a sample region 201 such that an optical path 203 exists between the sample region 201 and the image sensor 202. Notably, the sample region 201, image sensor 202, and optical path 203 are not required to be sealed in an imaging chamber. Light emitted from the sample region 201 (which can be light reflected off of, emission light from a sample within, or light transmitted or refracted through the sample region 201) can travel along the optical path 203 to be received by the image sensor 202. The image sensor 202 can be a CCD, a CMOS, or other such imager which is coupled to a TEC 204 which can thereby cool the image sensor 202 to maintain the image sensor 202 within an operating range. The TEC can draw thermal energy 226 (i.e. heat) from the image sensor 202 toward a heat sink 206. The heat sink 206 can disperse the thermal energy 226 or re-route the thermal energy 226 to another element of the image sensor system 200.

The image sensor 202 can be positioned to receive light along the optical path 203. In some aspects, the image sensor 202 can further include an image sensor cover 208 arranged to protect elements of the image sensor 202. In some embodiments, a sensor window 212 is positioned along the optical path 203 between the image sensor 202 and the sample region 201, where the sensor window 212 in part protects the image sensor 202 from foreign elements such as particulate matter or condensation. The sensor window 212 can be attached to the image sensor 202 with an adhesive element 210, along an edge of the image sensor 202 surrounding the image sensor cover 208. A thin film 214 can be further applied to the surface of the sensor window 212 distal from the image sensor 202 and proximate to the sample region 201. The thin film 214 can conduct electricity or thermal energy such that the thin film 214 can maintain a controlled temperature, further where the thin film 214 controlled temperature can be greater than an ambient or environmental temperature. In alternative aspects, the image sensor 202 can be provided without an image sensor cover 208.

In some aspects, the sensor window 212 can have a thickness of about one to about twenty millimeters (1 mm-20 mm), or any increment or gradient of thickness within that range. In particular aspects, the sensor window 212 can have a thickness of about five millimeters (5 mm). In further aspects, the sensor window 212 can be made of glass, having a coefficient of thermal expansion similar or proportion to the coefficient of thermal expansion for the image sensor 202. A glass used for the sensor window 212 can be a standard glass, or can be a glass doped with an element, such as boron (B) making a borosilicate glass, which can modify the index of refraction ($I_R$) or other transmissive characteristics of the sensor window 212. In other aspects, the sensor window 212 can be made of an optically transmissive polymer or plastic, where the polymer or plastic has a coefficient of thermal expansion similar or proportional to the coefficient of thermal expansion for the image sensor 202. In further aspects, the sensor window 212 can be made of a Pyrex glass, poly(methyl methacrylate) (PMMA or acrylic glass), polycarbonate, poly(vinyl chloride) (PVC), or polytetrafluoroethylene (PTFE).

In some aspects, the thin film 214 can be a thermally conductive thin film such as indium tin oxide (ITO). The thin film 214 can be applied to the sensor window by chemical vapor deposition, sputtering deposition, or other deposition methods known in the art. In some aspects, the thin film can be up to one hundred microns (100 μm) thick. The thin film 214 can be heated by electrical contacts 216 physically connected to the thin film 214. In some aspects, the electrical contacts 216 can be one or more point or linear resistive heaters. In other aspects, the electrical contacts 216 can be one or more circular or annular-shaped resistive heaters. Power can be delivered to the electrical contacts from a power source 218 through electrical connections 220, in some aspects forming a circuit. In various aspects, the power source 218 can be an alternating current or a direct current source, a battery, or conducted thermal energy 219 from the heat sink 206.

By heating the thin film 214 while the image sensor system 200 is in operation, the thin film 214 can be maintained at an elevated temperature 222 ($T_1$) that is greater than the ambient temperature 224 ($T_2$) of the image sensor system 200. The elevated temperature 222 of the thin film 214, relative to the ambient temperature 224, need only be sufficiently warmer to prevent condensation from forming on the surface of the thin film 214 and sensor window 212 surface coated by the thin film 214. In some aspects, the difference between the elevated temperature 222 and the ambient temperature 224 while the image sensor system 200 is in operation can be less than or equal to one degree centigrade ($\Delta T_{1-2} \leq 1°$ C.). In other aspects, the difference between the elevated temperature 222 and the ambient temperature 224 while the image sensor system 200 is in operation can be less than or equal to five degrees centigrade ($\Delta T_{1-2} \leq 5°$ C.). Accordingly, while the TEC 204 may draw thermal energy 226 away from the image sensor 202 in order to maintain operation of the image sensor 202 and/or a CCD or CMOS of the image sensor 202, the temperature of the sensor window 212 and thin film 214 facing the ambient environment of the image sensor system 200 does not drop such that condensation forms on the sensor window 212 in a manner that would occlude or disrupt light travelling long the optical path 203.

When heated, the sensor window 212 can both conduct heat and expand due to the heat. Accordingly, materials selected to construct the sensor window 212 can be selected to have or be within a range for, either or both of, a particular thermal conductivity ($\kappa$) and linear coefficient of thermal expansion ($\alpha_L$). The materials used for the sensor window 212 can be selected based on the size of the overall imaging apparatus, the projected operating ranges of temperature and light intensity of the imaging apparatus, or other design considerations. The thermal conductivity ($\kappa$) of the sensor window 212 can be used to determine how much heat is needed to provide to the thin film 214 in order to maintain an operating temperature above the ambient environmental temperature for the heated image sensor system 200. The linear coefficient of thermal expansion ($\alpha_L$) of the sensor window 212 can be used to determine the dimensions of the sensor window, and can be further selected to expand at a similar rate as the image sensor 202 to ensure the two elements remain coupled via the adhesive element 210.

In embodiments where the sensor window 212 is in direct contact with the image sensor cover 208, a difference in the index of refraction ($I_R$) between the two optical elements can lead to inaccurate detection of light received along the optical path 203. Accordingly, materials selected to construct the sensor window 212 can be selected to have or be within a range for a particular index of refraction which are close to or the same as the $I_R$ for image sensor cover 208, which can be a glass.

In alternative embodiments, the thin film 214 can be heated with a network of thermally conductive nanowires (not shown) disposed within the thin film 214. The nanowire network can be an optically transparent heater, which can be made of materials such as silver. The nanowire network can be arranged to be disposed randomly across the thin film 214 or with a regular or repeating pattern.

Exemplary values for the index of refraction ($I_R$), thermal conductivity ($\kappa$), and linear coefficient of thermal expansion ($\alpha_L$) for materials that can be used for the sensor window 212 are set forth in Table 1. The values and ranges for these material characteristics are instructive but not exclusive, as other materials can also be used to construct the sensor window 212. In some aspects, the sensor window 212 can have a thermal conductivity ($\kappa$) of about 0.04-1.14 W/(m*K). In other aspects, the sensor window 212 can have a linear coefficient of thermal expansion ($\alpha_L$) of about $3 \times 10^{-6}$-$80 \times 10^{-6}$ (1/K).

TABLE 1

| Material | Refractive Index $I_R$ | Thermal Conductivity $\kappa$ (W/(m * K)) | Coefficient of Linear Thermal Expansion $\alpha_L$ (1/K) |
|---|---|---|---|
| Polycarbonate | 1.584-1.586 | 0.19 | $37.5 \times 10^{-6}$-$37.65 \times 10^{-6}$ |
| PVC | 1.52-1.54 | 0.19 | $70 \times 10^{-6}$ |
| PMMA | 1.490-1.492 | 0.2 | $81 \times 10^{-6}$-$234 \times 10^{-6}$ |
| PTFE | 1.35-1.38 | 0.25 | $135 \times 10^{-6}$ |
| Pyrex glass | 1.474 | 1.005-1.05 | $4 \times 10^{-6}$-$5.9 \times 10^{-6}$ |
| Borosilicate glass | 1.474 | 1.14 | $3.3 \times 10^{-6}$ |

Figure 3:
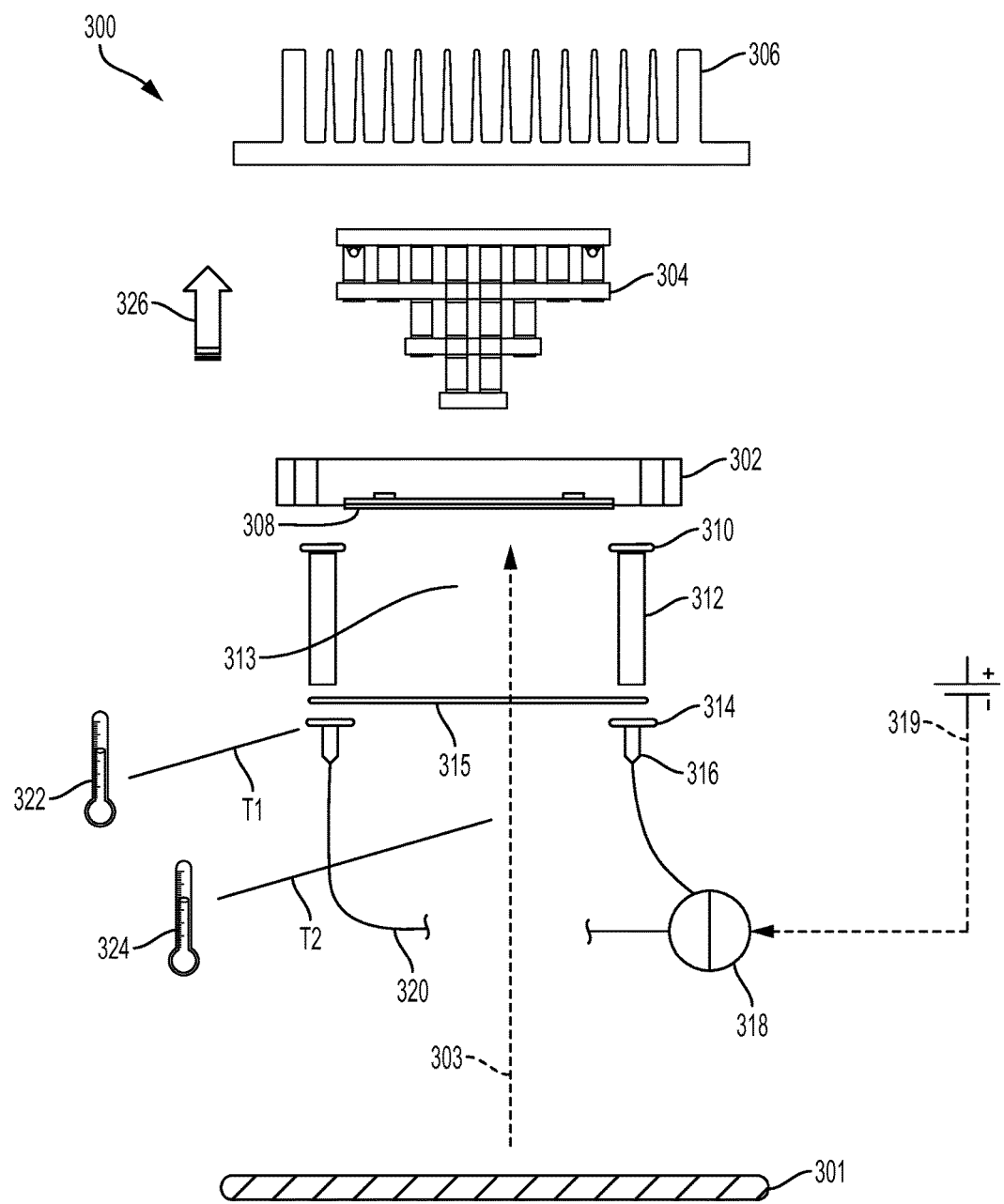
FIG. 3 is a schematic representing an exploded cross-sectional view of a configuration of elements for a heated image sensor system having a heating frame, according to some aspects or embodiments.

FIG. 3 is a schematic representing an exploded cross-sectional view of a configuration of elements for a heated image sensor system having a heating frame 300. The image sensor 302 can be positioned in relation to a sample region 301 such that an optical path 303 exists between the sample region 301 and the image sensor 302. Also in this embodiment, the sample region 301, image sensor 302, and optical path 303 are not required to be sealed in an imaging chamber. Light emitted from the sample region 301 (which can be light reflected off of, emission light from a sample within, or light transmitted or refracted through the sample region 301) can travel along the optical path 303 to be received by the image sensor 302. The image sensor 302 can be a CCD, CMOS, or other such sensory element which is coupled to a TEC 304 which can cool the image sensor 302 to maintain the image sensor 302 within an operating range. The TEC can draw thermal 326 from the image sensor 302 toward a heat sink 306. The heat sink 306 can disperse the thermal energy 326 or re-route the thermal energy 326 to another element of the image sensor system 300.

The image sensor 302 can be positioned to receive light along the optical path 303. In some aspects, the image sensor 302 can further include an image sensor cover 308 arranged to protect elements of the image sensor 302. In some embodiments, a heating frame 312 is positioned encircling at least a portion of the optical path 303 between the image sensor 302 and the sample region 301 along the optical path 303 between the image sensor 302 and the sample region 301. The heating frame 312 can be attached to the image sensor 302 with an adhesive element 310, along an edge of the image sensor 302 surrounding the image sensor cover 308. A secondary layer 315 can be coupled to the heating frame 312, and can be operable to prevent condensation in the ambient atmosphere from reaching and condensing on the image sensor 302. A thin film 314 can be further applied to the surface of the secondary layer 315, distal from the image sensor 302 and proximate to the sample region 301. The secondary layer can be made of a Pyrex glass, poly(methyl methacrylate) (PMMA or acrylic glass), polycarbonate, poly(vinyl chloride) (PVC), or polytetrafluoroethylene (PTFE), as either a single piece or as a multi-piece component. The thin film 314 can conduct electricity or thermal energy such that the thin film 314 can maintain a controlled temperature, where the thin film 314 can be controlled at a temperature that can be greater than an ambient or environmental temperature. In alternative aspects, the image sensor 302 can be provided without an image sensor cover 308.

In some aspects, the heating frame 312 can be made of a metal, a plastic, a Pyrex glass, PMMA, acrylic glass, polycarbonate, PVC, or PTFE. In other aspects, the heating frame 312 can be made of a single structural element or multiple structural elements (e.g. individual legs or walls) bound to the image sensor 302. The heating frame 312 can have a thickness of about one to twenty millimeters (1 mm-20 mm). In particular aspects, the heating frame 312 can have a thickness of about five millimeters (5 mm). The heating frame 312 can define an insulating space 313 having a temperature relatively greater than the ambient temperature around the image sensor system 300. In some embodiments, the secondary layer 315 can have a thickness of about from 0.7 mm to about seven millimeters (7 mm).

In some aspects, the thin film 314 can be a thermally conductive thin film such as indium tin oxide (ITO). The thin film 314 can be applied to an edge of the heating frame 312 and/or the secondary layer 315 by chemical vapor deposition, sputtering deposition, or other deposition methods known in the art. In some aspects, the thin film 314 can be up to one hundred microns (100 μm) thick. The thin film 314 can be heated by electrical contacts 316 physically connected to the thin film 314. In some aspects, the electrical contacts 316 can be one or more point or linear resistive heaters. In other aspects, the electrical contacts 316 can be one or more circular or annular-shaped resistive heaters, matching to the structure and profile of the heating frame 312. Power can be delivered to the electrical contacts from a power source 318 through electrical connections 320, in some aspects forming a circuit. In various aspects, the power source 318 can be an alternating current or a direct current source, a battery 319, or conducted thermal energy from the heat sink 306.

By heating the thin film 314 while the image sensor system 300 is in operation, the thin film 314 can be maintained at an elevated temperature 322 ($T_1$) that is greater than the ambient temperature 324 ($T_2$) of the image sensor system 300. The elevated temperature 322 of the thin film 314, relative to the ambient temperature 324, need only be sufficiently warmer to prevent condensation from forming on the surface of the secondary layer 315, image sensor 302, or image sensor cover 308. In particular, the thin film 314 when heated raises the temperature of the insulating space 313 relative to the ambient temperature 324. In some aspects, the difference between the elevated temperature 322 and the ambient temperature 324 while the image sensor system 300 is in operation can be less than or equal to one degree centigrade ($\Delta T_{1-2} \leq 1°$ C.). In other aspects, the difference between the elevated temperature 322 and the ambient temperature 324 while the image sensor system 300 is in operation can be less than or equal to five degrees centigrade ($\Delta T_{1-2} \leq 5°$ C.). Accordingly, while the TEC 304 may draw thermal energy 326 away from the image sensor 302 in order to maintain operation of the image sensor 302 and/or a CCD or CMOS of the image sensor 302, the temperature of the insulating space 313 does not drop such that condensation forms on the image sensor 302 or image sensor cover 308 in a manner that would occlude or disrupt light travelling long the optical path 303.

Figure 4A:
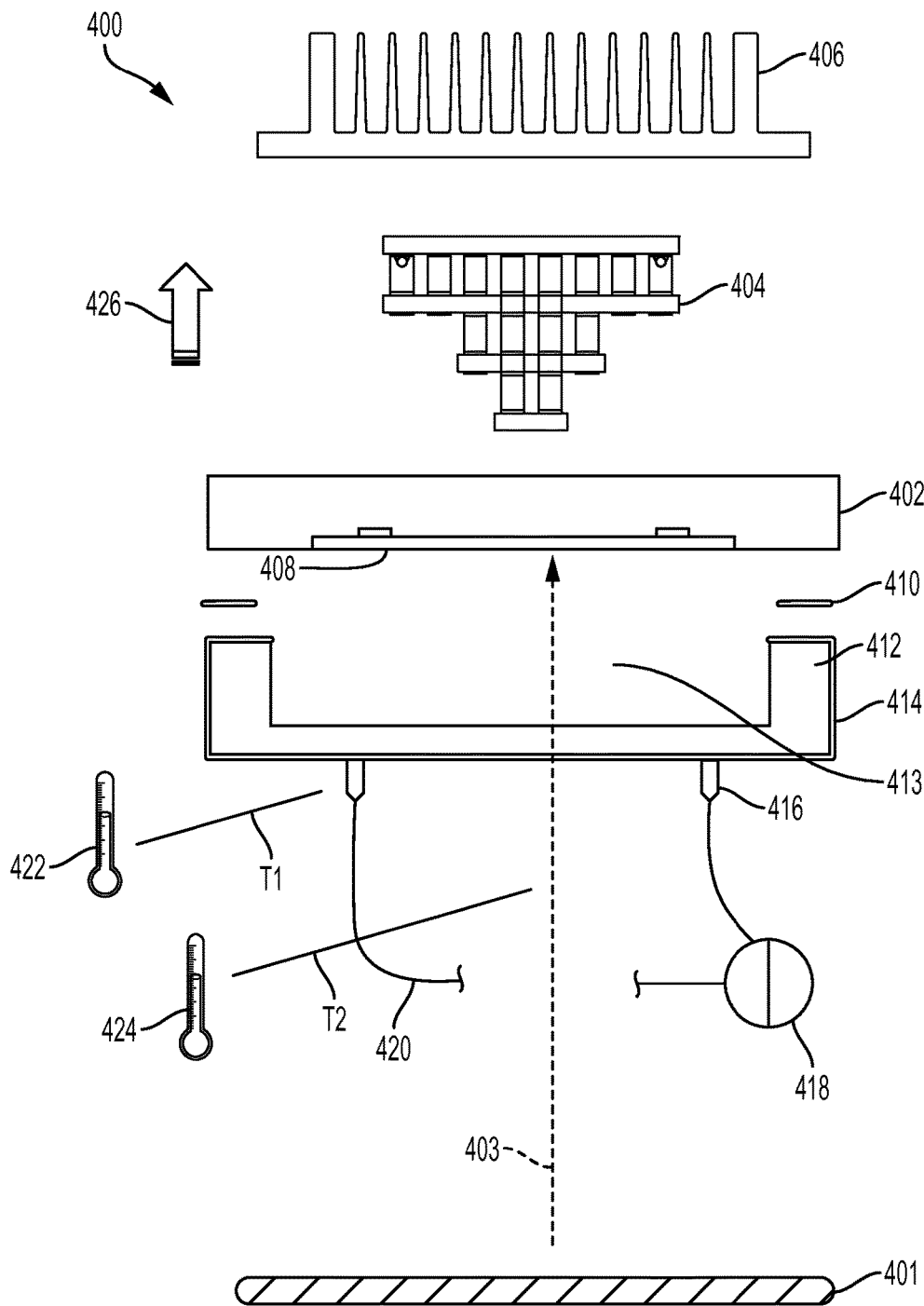
FIG. 4A is a schematic representing an exploded cross-sectional view of a configuration of elements for a heated image sensor system having a concave sensor window with an insulation cavity, according to some aspects or embodiments.

FIG. 4A is a schematic representing an exploded cross-sectional view of a configuration of elements for a heated image sensor system having a concave sensor window with an insulation cavity 400. The image sensor 402 can be positioned in relation to a sample region 401 such that an optical path 403 exists between the sample region 401 and the image sensor 402. Again, in such embodiments, the sample region 401, image sensor 402, and optical path 403 are not required to be sealed in an imaging chamber. Light emitted from the sample region 401 (which can be light reflected off of, emission light from a sample within, or light transmitted or refracted through the sample region 401) can travel along the optical path 403 to be received by the image sensor 402. The image sensor 402 can be a CCD, CMOS, or other such sensory element which is coupled to a TEC 404 which can cool the image sensor 402 to maintain the image sensor 402 within an operating range. The TEC can draw thermal 426 from the image sensor 402 toward a heat sink 406. The heat sink 406 can disperse the thermal energy 426 or re-route the thermal energy 426 to another element of the image sensor system 400.

The image sensor 402 can be positioned to receive light along the optical path 403. In some aspects, the image sensor 402 can further include an image sensor cover 408 arranged to protect elements of the image sensor 402. In some embodiments, a concave sensor window 412 is positioned along the optical path 403 between the image sensor 402 and the sample region 401, where the concave sensor window 412 in part protects the sensory element 408 from foreign elements such as particulate matter or condensation. The concavity of the concave sensor window 412 faces the image sensor 402 and sensory element 408, forming a window cavity 413 space in front of the sensory element 408. The concave sensor window 412 can be attached to the image sensor 402 with an adhesive element 410, along an edge of the image sensor 402 surrounding the sensory element 408. A thin film 414 can be further applied to the surface of the concave sensor window 412 distal from the image sensor 402 and proximate to the sample region 401. The thin film 414 can conduct electricity or thermal energy such that the thin film 414 can maintain a controlled temperature, further where the thin film 414 controlled temperature can be greater than an ambient or environmental temperature. In alternative aspects, the image sensor 402 can be provided without an image sensor cover 408.

In some aspects, the concave sensor window 412 can be made of glass having an overall thickness of about one to twenty millimeters (1 mm-20 mm), or any increment or gradient of thickness within that range. The window cavity 413 can have a depth, extending into the sensor window 412, of about one to nineteen millimeters (1 mm-19 mm), In particular aspects, the concave sensor window 412 can have an overall thickness of about five millimeters (5 mm). In other particular aspects, the window cavity 413 can have a depth, extending into the sensor window 412, of about one to four millimeters (1 mm-4 mm). The window cavity 413 can have a width, extending across the center of the sensor window 412, that is from about 10% to 90% the width of the overall sensor window 412. A glass used for the concave sensor window 412 can be a standard glass, or can be a glass doped with an element, such as boron (B) making a borosilicate glass, which can modify the index of refraction ($I_R$) or other transmissive characteristics of the concave sensor window 412. In other aspects, the concave sensor window 412 can be made of an optically transmissive polymer or plastic, where the polymer or plastic has a coefficient of thermal expansion similar to glass, or a coefficient of thermal expansion similar to the coefficient of thermal expansion for the image sensor 402. In further aspects, the concave sensor window 412 can be made of a Pyrex glass, poly (methyl methacrylate) (PMMA or acrylic glass), polycarbonate, poly(vinyl chloride) (PVC), or polytetrafluoroethylene (PTFE). In various aspects, the concave sensor window 412 can be formed as either a single piece or as a multi-piece component.

In further aspects, the window cavity 413, being a sealed space once the sensor window 412 is coupled to the image sensor 402 via the adhesive element 410, can hold a vacuum or a gas. In aspects, the gas held within the window cavity 413 can be standard air, an inert gas, or the like. The window cavity 413 can thereby function as an insulation cavity, regulating the rate of thermal change directly in front of the image sensor 402 and image sensor cover 408, maintaining an operational temperature in that space. A gas held within the window cavity 413 can be configured or selected to minimize any difference in the index of refraction ($I_R$) between the material of the concave sensor window 412 and the gas within the window cavity 413, thereby reducing refraction or deflection of the optical path 403 as light passes through the concave sensor window 412 and window cavity 413. In some aspects, the concave sensor window 412 can further include an anti-reflective coating, thereby reducing refraction or deflection of the optical path 403 as light passes through the concave sensor window 412. In some aspects, the side of concave sensor window 412 distal from the image sensor 402 and proximate to the sample region 401 can be generally planar.

In some aspects, the thin film 414 can be a thermally conductive thin film such as indium tin oxide (ITO). The thin film 414 can be applied to the sensor window by chemical vapor deposition, sputtering deposition, or other deposition methods known in the art. In some aspects, the thin film can be up to one hundred microns (100 μm) thick. The thin film 414 can be heated by electrical contacts 416 physically connected to the thin film 414. In some aspects, the electrical contacts 416 can be one or more point or linear resistive heaters. In other aspects, the electrical contacts 416 can be one or more circular or annular-shaped resistive heaters. Power can be delivered to the electrical contacts from a power source 418 through electrical connections 420, in some aspects forming a circuit. In various aspects, the power source 418 can be an alternating current or a direct current source, a battery, or conducted thermal energy from the heat sink 406.

By heating the thin film 414 while the image sensor system 400 is in operation, the thin film 414 can be maintained at an elevated temperature 422 ($T_1$) that is greater than the ambient temperature 424 ($T_2$) of the image sensor system 400. The elevated temperature 422 of the thin film 414, relative to the ambient temperature 424 need only be sufficiently warmer to prevent condensation from forming on the surface of the thin film 414 and concave sensor window 412 surface coated by the thin film 414. In some aspects, the difference between the elevated temperature 422 and the ambient temperature 424 while the image sensor system 400 is in operation can be less than or equal to one degree centigrade ($\Delta T_{1-2} \leq 1°$ C.). In other aspects, the difference between the elevated temperature 422 and the ambient temperature 424 while the image sensor system 400 is in operation can be less than or equal to five degrees centigrade ($\Delta T_{1-2} \leq 5°$ C.). Accordingly, while the TEC 404 may draw thermal energy 426 away from the image sensor 402 in order to maintain operation of the image sensor 402, CMOS, and/or a CCD of the image sensor 402, the temperature of the sensor window 412 and thin film 414 facing the ambient environment of the image sensor system 400 does not drop such that condensation forms on the concave sensor window 412 in a manner that would occlude or disrupt light travelling long the optical path 403.

When heated, the concave sensor window 412 can both conduct heat and expand due to the heat. Accordingly, materials selected to construct the concave sensor window 412 can be selected to have or be within a range for, either or both of, a particular thermal conductivity (κ) and linear coefficient of thermal expansion ($\alpha_L$). The materials used for the concave sensor window 412 can be selected based on the size of the overall imaging apparatus, the projected operating ranges of temperature and light intensity of the imaging apparatus, or other design considerations. The thermal conductivity (κ) of the concave sensor window 412 can be used to determine how much heat is needed to provide to the thin film 414 in order to maintain an operating temperature above the ambient environmental temperature for the heated image sensor system 400. The linear coefficient of thermal expansion ($\alpha_L$) of the concave sensor window 412 can be used to determine the dimensions of the sensor window, and can be further selected to expand at a similar rate as the image sensor 402 to ensure the two elements remain coupled via the adhesive element 410. Materials and characteristics of such materials that can be used to form the concave sensor window 412 are set forth in Table 1 above. The values and ranges for these material characteristics are instructive but not exclusive, as other materials can also be used to construct the concave sensor window 412. In some aspects, the concave sensor window 412 can have a thermal conductivity (κ) of about 0.04-1.14 W/(m*K). In other aspects, the concave sensor window 412 can have a linear coefficient of thermal expansion ($\alpha_L$) of about $3 \times 10^{-6}$-$80 \times 10^{-6}$(1/K).

The structure of the concave window sensor 412 can be further configured to aid heat conduction. In some aspects, the walls of the concave window sensor 412, being the portion of the concave window sensor 412 defining the depth of the window cavity 413, can be configured to be thin relative to other aspects of the heated image sensor system 400 to have a reduced overall heat capacity and to efficiently conduct heat to or through the thin film 414. The walls of the concave window sensor 412 can be from about one millimeter (1 mm) to about five millimeters (5 mm) thick, or have a thickness at any increment or gradient within that range. Similarly, the side of the concave window sensor 412 proximate to the sensor region 401 can be from about one millimeter (1 mm) to about five millimeters (5 mm) thick, or have a thickness at any increment or gradient within that range. In such aspects, the walls of the concave window sensor 412 and the side of the concave window sensor 412 proximate to the sensor region 401 can be designed to maintain the structural integrity needed for the concave window sensor 412. The thickness of the concave window sensor 412 can be, in part, dependent on the material used to construct a particular concave window sensor 412.

Figure 4B:
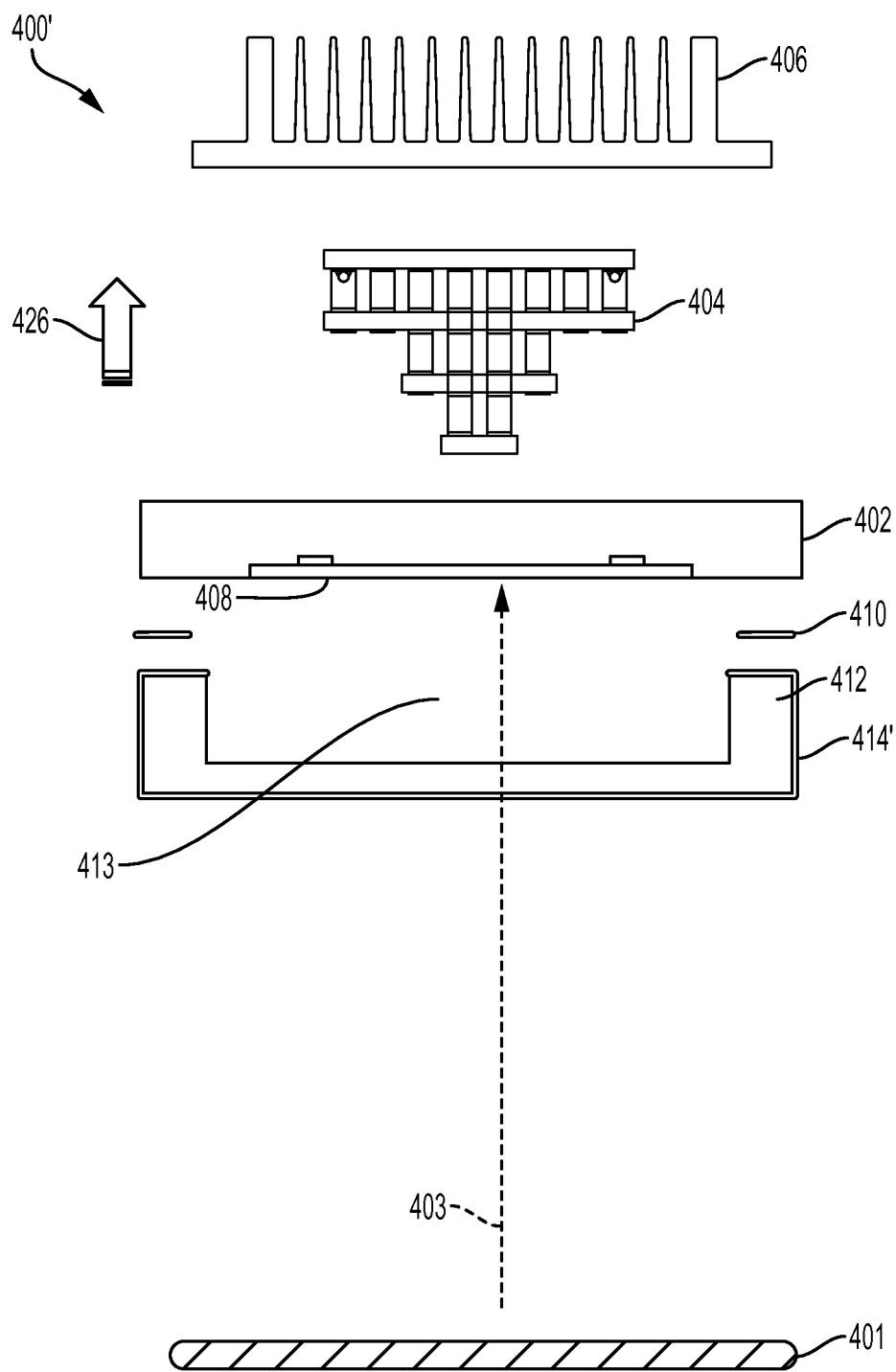
FIG. 4B is a schematic representing an exploded cross-sectional view of a configuration of elements for an image sensor system having a concave sensor window with an insulation cavity, according to some aspects or embodiments.

FIG. 4B is a schematic representing an exploded cross-sectional view of a configuration of elements for an image sensor system having a concave sensor window with an insulation cavity 400'. As in FIG. 4A, the image sensor 402 can be positioned in relation to a sample region 401 such that the optical path 403 exists between the sample region 401 and the image sensor 402, where the sample region 401, image sensor 402, and optical path 403 are not required to be sealed in an imaging chamber. Light emitted from the sample region 401 can travel along the optical path 403 to be received by the image sensor 402. The image sensor 402 can be a CCD, CMOS, or other such sensory element which is coupled to a TEC 404 which can cool the image sensor 402 to maintain the image sensor 402 within an operating range. The TEC can draw thermal 426 from the image sensor 402 toward a heat sink 406, where the heat sink 406 can disperse the thermal energy 426. The image sensor 402 can further include a image sensor cover 408, where the image sensor 402 is positioned to receive light along the optical path 403. In some embodiments, a concave sensor window 412 is positioned along the optical path 403 between the image sensor 402 and the sample region 401, where the concave sensor window 412 in part protects the image sensor 402 from foreign elements such as particulate matter or condensation. The concavity of the concave sensor window 412 faces the image sensor 402 and image sensor cover 408, forming the window cavity 413 space in front of the image sensor cover 408. The concave sensor window 412 can be attached to the image sensor 402 with an adhesive element 410, along an edge of the image sensor 402 surrounding the image sensor cover 408.

In some aspects, the thin film 414' can be further applied to the surface of the concave sensor window 412 distal from the image sensor 402 and proximate to the sample region 401, where the thin film 414' is an anti-condensation (or anti-fog) coating. The presence of the anti-condensation thin film 414' can prevent condensation from forming on the sensor window 412 or on the anti-condensation thin film 414' without the need to conduct heat into the anti-condensation thin film 414' or through the concave sensor window 412. The anti-condensation thin film 414' can be further configured or selected to have anti-reflective properties, to allow light to pass through along the optical path 403 without adversely distorting the optical path 403 to the image sensor 402.

In various embodiments set forth below, any of the configurations illustrated in FIG. 4C, 4D, 4E, 4F, or 4G can include a heating control system as shown in FIG. 4A. In other words, the power source 418 as shown in FIG. 4A, drawing power from a heat sink 406, a battery, or an other power source, can be optionally applied to connect to the thin film 414 shown in FIG. 4C, 4D, 4E, 4F, or 4G using electrical contacts 416 as disclosed herein. Alternatively, any of the configurations illustrated in FIG. 4C, 4D, 4E, 4F, or 4G can include an anti-condensation thin film 414' without the use of a heating control system, as shown in FIG. 4B.

Figure 4C:
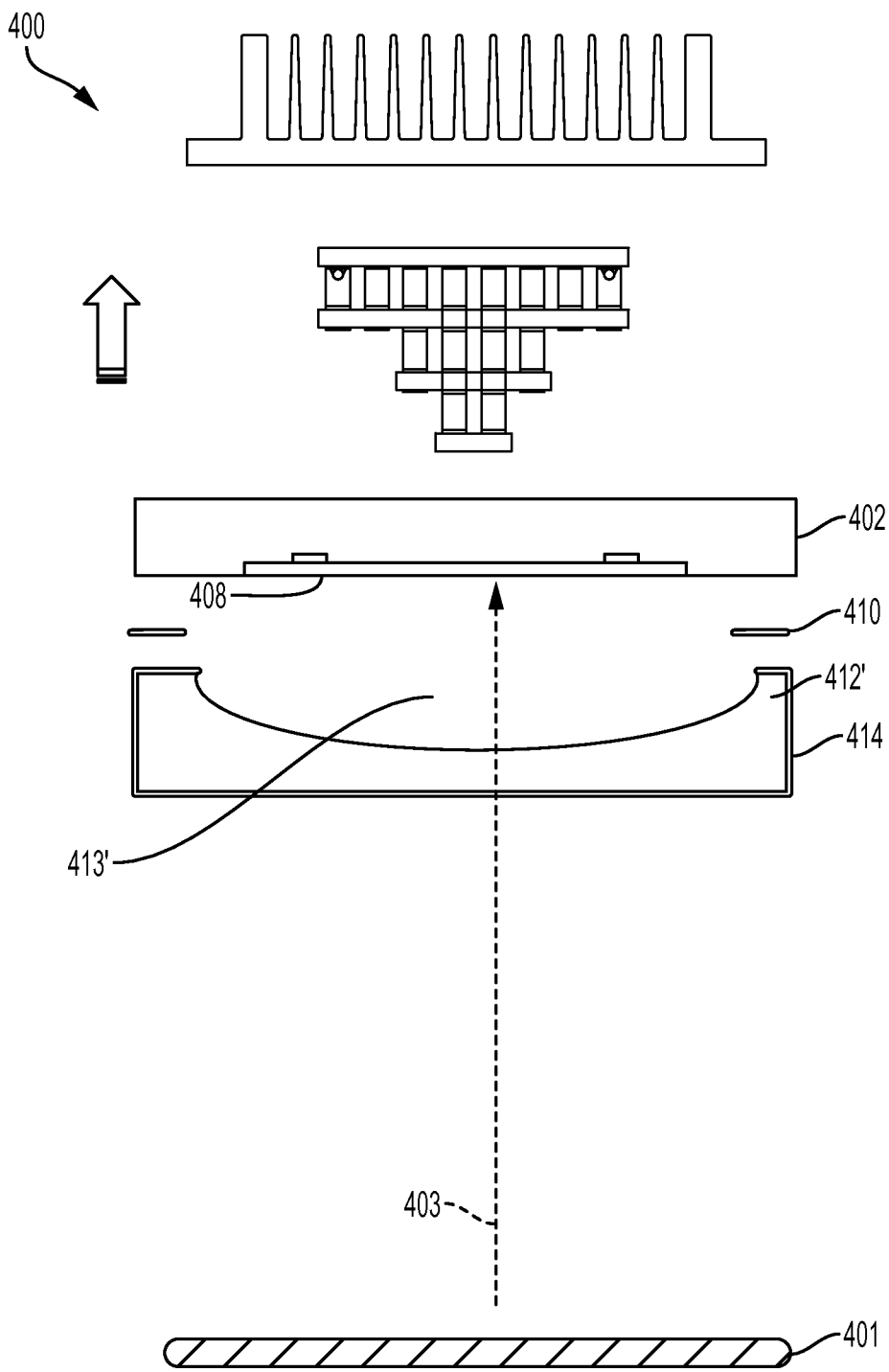
FIG. 4C is a schematic representing an exploded cross-sectional view of a configuration of elements for an image sensor system having an curved concave sensor window with an insulation cavity, according to some aspects or embodiments.

FIG. 4C is a schematic representing an exploded cross-sectional view of a configuration of elements for an image sensor system 400 having a curved concave sensor window 412' with an insulation cavity. (As used herein, the adjective "curved" used for the term "curved concave sensor window" refers to the internal curve of a window cavity facing an image sensor.) As in FIG. 4A, the image sensor 402 can be positioned in relation to a sample region 401 such that the optical path 403 exists between the sample region 401 and the image sensor 402, where the sample region 401, image sensor 402, and optical path 403 are not required to be sealed in an imaging chamber. Light emitted from the sample region 401 can travel along the optical path 403 to be received by the image sensor 402. The image sensor 402 can be a CCD, CMOS, or other such sensory element which is coupled to a TEC 404 which can cool the image sensor 402 to maintain the image sensor 402 within an operating range. The TEC can draw thermal 426 from the image sensor 402 toward a heat sink 406, where the heat sink 406 can disperse the thermal energy 426. The image sensor 402 can further include an image sensor cover 408, where the image sensor 402 is positioned to receive light along the optical path 403. In such embodiments, a curved concave sensor window 412' is positioned along the optical path 403 between the image sensor 402 and the sample region 401, where the curved concave sensor window 412' in part protects the image sensor 402 from foreign elements such as particulate matter or condensation. The concavity of the curved concave sensor window 412' faces the image sensor 402 and image sensor cover 408, forming the window cavity 413 space in front of the image sensor cover 408. The curved concave sensor window 412' can be attached to the image sensor 402 with an adhesive element 410, along an edge of the image sensor 402 surrounding the image sensor cover 408.

The curvature of the curved concave sensor window 412' can be configured to focus light incident from the sample region along the optical path 403 in a direction toward a specific region of the image sensor 402 or image sensor cover 408. The curvature of the curved concave sensor window 412' can allow for more precise measurement of a light signal received along the optical path 403, and can account for reflective, diffractive, or refractive effects of the material selected to construct the curved concave sensor window 412' and the thicknesses thereof.

In embodiments where heated, the curved concave sensor window 412' can both conduct heat and expand due to the heat. Accordingly, materials selected to construct the curved concave sensor window 412' can be selected to have or be within a range for, either or both of, a particular thermal conductivity ($\kappa$) and linear coefficient of thermal expansion ($\alpha_L$). The materials used for the curved concave sensor window 412' can be selected based on the size of the overall imaging apparatus, the projected operating ranges of temperature and light intensity of the imaging apparatus, or other design considerations. The thermal conductivity ($\kappa$) of the curved concave sensor window 412' can be used to determine how much heat is needed to provide to the thin film 414 in order to maintain an operating temperature above the ambient environmental temperature for the heated image sensor system 400. The linear coefficient of thermal expansion ($\alpha_L$) of the curved concave sensor window 412' can be used to determine the dimensions of the sensor window, and can be further selected to expand at a similar rate as the image sensor 402 to ensure the two elements remain coupled via the adhesive element 410. Materials and characteristics of such materials that can be used to form the curved concave sensor window 412' are set forth in Table 1 above. The values and ranges for these material characteristics are instructive but not exclusive, as other materials can also be used to construct the curved concave sensor window 412'. In some aspects, the curved concave sensor window 412' can have a thermal conductivity ($\kappa$) of about 0.04-1.14 W/(m*K). In other aspects, the curved concave sensor window 412' can have a linear coefficient of thermal expansion ($\alpha_L$) of about $3 \times 10^{-6}$-$80 \times 10^{-6}$(1/K).

Figure 4D:
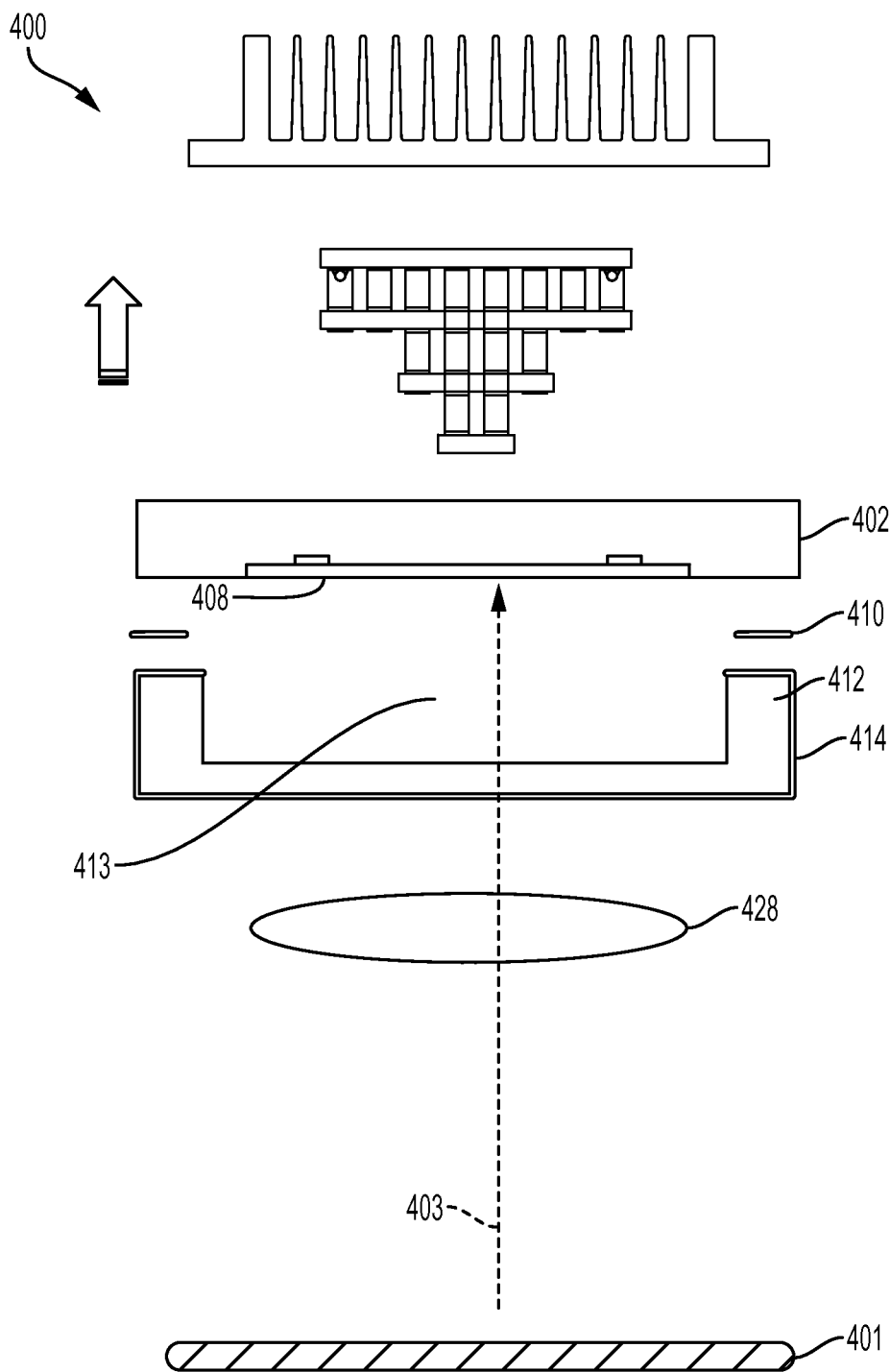
FIG. 4D is a schematic representing an exploded cross-sectional view of a configuration of elements for an image sensor system having a lens and a concave sensor window with an insulation cavity, according to some aspects or embodiments.

FIG. 4D is a schematic representing an exploded cross-sectional view of a configuration of elements for an image sensor system 400 having a lens 428 and a concave sensor window 412 with an insulation cavity. As in FIG. 4A, the image sensor 402 can be positioned in relation to a sample region 401 such that the optical path 403 exists between the sample region 401 and the image sensor 402, passing through the lens 428. In such aspects, the sample region 401, image sensor 402, lens 428, and optical path 403 are not required to be sealed in an imaging chamber. Light emitted from the sample region 401 can travel along the optical path 403 to be received by the image sensor 402. The image sensor 402 can be a CCD, CMOS, or other such sensory element which is coupled to a TEC 404 which can cool the image sensor 402 to maintain the image sensor 402 within an operating range. The TEC can draw thermal 426 from the image sensor 402 toward a heat sink 406, where the heat sink 406 can disperse the thermal energy 426. The image sensor 402 can further include an image sensor cover 408, where the image sensor 402 is positioned to receive light along the optical path 403. In such embodiments, a concave sensor window 412 is positioned along the optical path 403 between the image sensor 402 and the sample region 401, where the concave sensor window 412 in part protects the image sensor 402 from foreign elements such as particulate matter or condensation. The concavity of the concave sensor window 412 faces the image sensor 402 and image sensor cover 408, forming the window cavity 413 space in front of the image sensor cover 408. The concave sensor window 412 can be attached to the image sensor 402 with an adhesive element 410, along an edge of the image sensor 402 surrounding the image sensor cover 408.

The lens 428 can be configured or positioned along the optical path 403 to focus light incident from the sample region along the optical path 403, through the concave sensor window 412, in a direction toward a specific region of the image sensor 402 or image sensor cover 408. The curvature of lens 428 can allow for more precise measurement of a light signal received along the optical path 403, and can account for reflective, diffractive, or refractive effects of the material selected to construct the concave sensor window 412 and the thicknesses thereof.

In embodiments where heated, the concave sensor window 412 of FIG. 4D can both conduct heat and expand due to the heat as discussed in relation to FIG. 4A above.

Figure 4E:
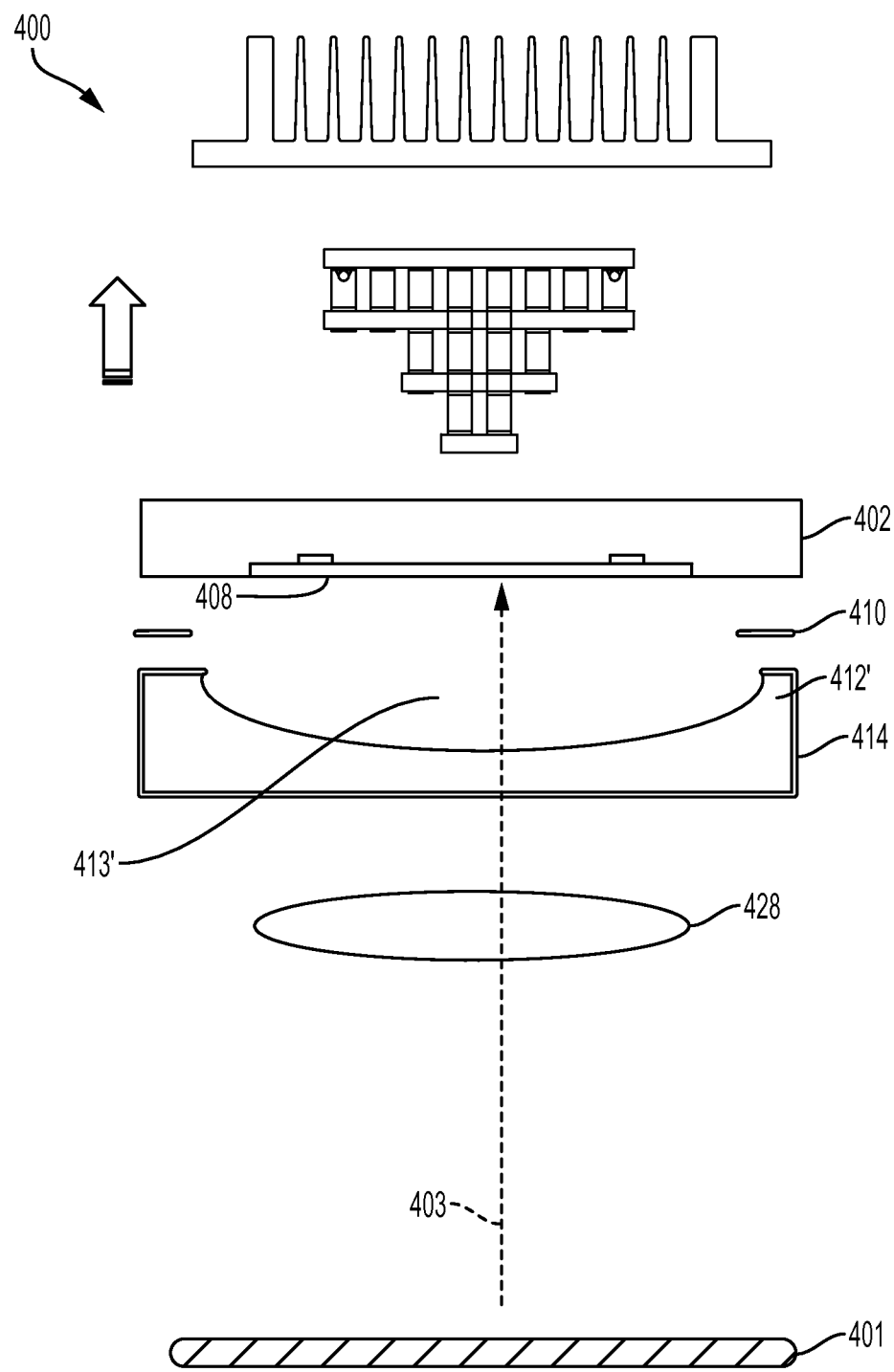
FIG. 4E is a schematic representing an exploded cross-sectional view of a configuration of elements for an image sensor system having a lens and a curved concave sensor window with an insulation cavity, according to some aspects or embodiments.

FIG. 4E is a schematic representing an exploded cross-sectional view of a configuration of elements for an image sensor system 400 having a lens 428 and a curved concave sensor window 412' with an insulation cavity. As in FIG. 4A, the image sensor 402 can be positioned in relation to a sample region 401 such that the optical path 403 exists between the sample region 401 and the image sensor 402, passing through the lens 428. In such aspects, the sample region 401, image sensor 402, lens 428, and optical path 403 are not required to be sealed in an imaging chamber. Light emitted from the sample region 401 can travel along the optical path 403 to be received by the image sensor 402. The image sensor 402 can be a CCD, CMOS, or other such sensory element which is coupled to a TEC 404 which can cool the image sensor 402 to maintain the image sensor 402 within an operating range. The TEC can draw thermal 426 from the image sensor 402 toward a heat sink 406, where the heat sink 406 can disperse the thermal energy 426. The image sensor 402 can further include an image sensor cover 408, where the image sensor 402 is positioned to receive light along the optical path 403. In such embodiments, a curved concave sensor window 412' is positioned along the optical path 403 between the image sensor 402 and the sample region 401, where the curved concave sensor window 412' in part protects the image sensor 402 from foreign elements such as particulate matter or condensation. The concavity of the curved concave sensor window 412' faces the image sensor 402 and image sensor cover 408, forming the window cavity 413 space in front of the image sensor cover 408. The curved concave sensor window 412' can be attached to the image sensor 402 with an adhesive element 410, along an edge of the image sensor 402 surrounding the image sensor cover 408.

The curvatures of the curved concave sensor window 412' and the lens 428 can be configured to operate in tandem, to focus light incident from the sample region along the optical path 403 in a direction toward a specific region of the image sensor 402 or image sensor cover 408. The curvatures and interaction of the curved concave sensor window 412' and lens 428 can allow for more precise measurement of a light signal received along the optical path 403, and can account for reflective, diffractive, or refractive effects of the material selected to construct the curved concave sensor window 412 and the thicknesses thereof.

In embodiments where heated, the concave sensor window 412 of FIG. 4E can both conduct heat and expand due to the heat as discussed in relation to FIG. 4A above.

Figure 4F:
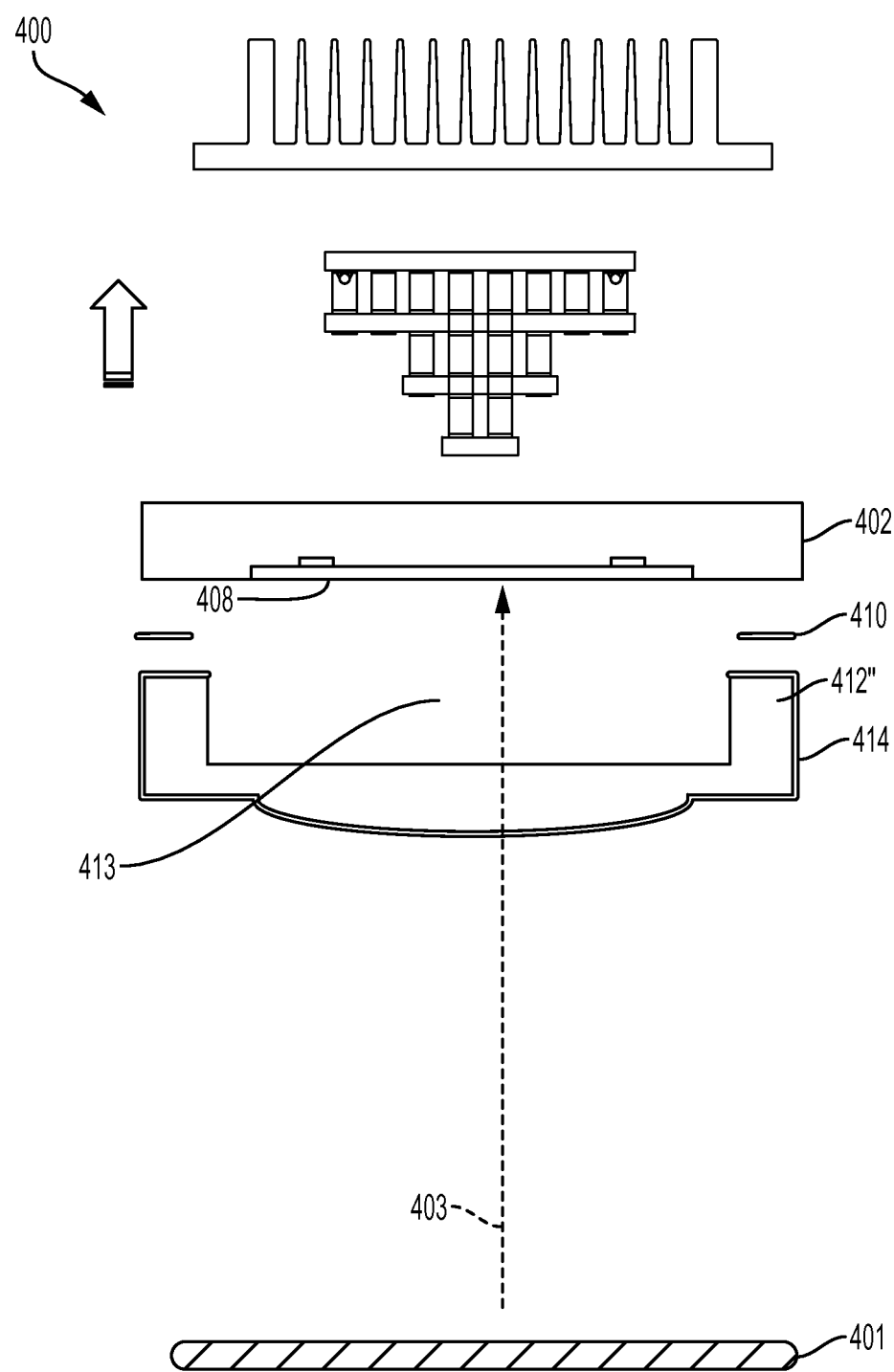
FIG. 4F is a schematic representing an exploded cross-sectional view of a configuration of elements for an image sensor system having a bulged concave sensor window with an insulation cavity, according to some aspects or embodiments.

FIG. 4F is a schematic representing an exploded cross-sectional view of a configuration of elements for an image sensor system having a bulged concave sensor window 412" with an insulation cavity. (As used herein, the adjective "bulged" used for the term "bulged concave sensor window" refers to the projecting surface of a sensor window proximate to and facing a sample region.) As in FIG. 4A, the image sensor 402 can be positioned in relation to a sample region 401 such that the optical path 403 exists between the sample region 401 and the image sensor 402, where the sample region 401, image sensor 402, and optical path 403 are not required to be sealed in an imaging chamber. Light emitted from the sample region 401 can travel along the optical path 403 to be received by the image sensor 402. The image sensor 402 can be a CCD, CMOS, or other such sensory element which is coupled to a TEC 404 which can cool the image sensor 402 to maintain the image sensor 402 within an operating range. The TEC can draw thermal 426 from the image sensor 402 toward a heat sink 406, where the heat sink 406 can disperse the thermal energy 426. The image sensor 402 can further include an image sensor cover 408, where the image sensor 402 is positioned to receive light along the optical path 403. In such embodiments, a bulged concave sensor window 412" is positioned along the optical path 403 between the image sensor 402 and the sample region 401, where the bulged concave sensor window 412" in part protects the image sensor 402 from foreign elements such as particulate matter or condensation. The concavity of the bulged concave sensor window 412" faces the image sensor 402 and image sensor cover 408, forming the window cavity 413 space in front of the image sensor cover 408. The bulged concave sensor window 412" can be attached to the image sensor 402 with an adhesive element 410, along an edge of the image sensor 402 surrounding the image sensor cover 408.

The curvature of the bulged concave sensor window 412" can be configured to focus light incident from the sample region along the optical path 403 in a direction toward a specific region of the image sensor 402 or image sensor cover 408. The curvature of the bulged concave sensor window 412" allow for more precise measurement of a light signal received along the optical path 403, and can account for reflective, diffractive, or refractive effects of the material selected to construct the bulged concave sensor window 412" and the thicknesses thereof. In alternative aspects, the bulged concave sensor window 412" can be used in a system that further includes a lens 428 element as shown in FIGS. 4D and 4E.

In embodiments where heated, the bulged concave sensor window 412" can both conduct heat and expand due to the heat. Accordingly, materials selected to construct the bulged concave sensor window 412" can be selected to have or be within a range for, either or both of, a particular thermal conductivity ($\kappa$) and linear coefficient of thermal expansion ($\alpha_L$). The materials used for the bulged concave sensor window 412" can be selected based on the size of the overall imaging apparatus, the projected operating ranges of temperature and light intensity of the imaging apparatus, or other design considerations. The thermal conductivity ($\kappa$) of the bulged concave sensor window 412" can be used to determine how much heat is needed to provide to the thin film 414 in order to maintain an operating temperature above the ambient environmental temperature for the heated image sensor system 400. The linear coefficient of thermal expansion ($\alpha_L$) of the bulged concave sensor window 412" can be used to determine the dimensions of the sensor window, and can be further selected to expand at a similar rate as the image sensor 402 to ensure the two elements remain coupled via the adhesive element 410. Materials and characteristics of such materials that can be used to form the bulged concave sensor window 412" are set forth in Table 1 above. The values and ranges for these material characteristics are instructive but not exclusive, as other materials can also be used to construct the bulged concave sensor window 412". In some aspects, the bulged concave sensor window 412" can have a thermal conductivity (κ) of about 0.04-1.14 W/(m*K). In other aspects, the curved concave sensor window 412' can have a linear coefficient of thermal expansion ($\alpha_L$) of about $3 \times 10^{-6}$-$80 \times 10^{-6}$(1/K).

Figure 4G:
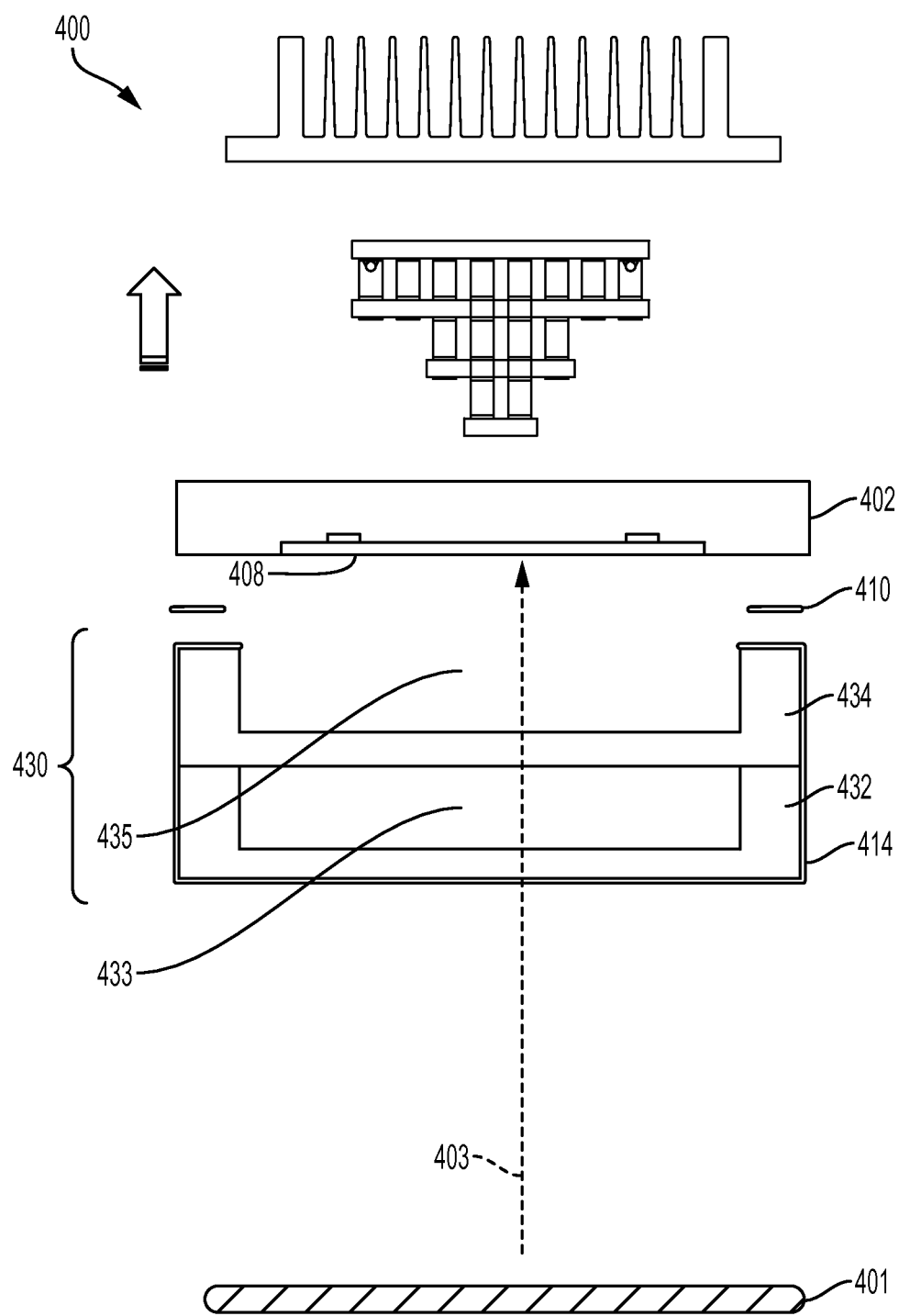
FIG. 4G is a schematic representing an exploded cross-sectional view of a configuration of elements for an image sensor system having a doubled concave sensor window structure with insulation cavities, according to some aspects or embodiments.

FIG. 4G is a schematic representing an exploded cross-sectional view of a configuration of elements for an image sensor system 400 having a doubled concave sensor window structure 430 with insulation cavities. The image sensor 402 can be positioned in relation to a sample region 401 such that an optical path 403 exists between the sample region 401 and the image sensor 402. Again, in such embodiments, the sample region 401, image sensor 402, and optical path 403 are not required to be sealed in an imaging chamber. Light emitted from the sample region 401 (which can be light reflected off of, emission light from a sample within, or light transmitted or refracted through the sample region 401) can travel along the optical path 403 to be received by the image sensor 402. The image sensor 402 can be a CCD, CMOS, or other such sensory element which is coupled to a TEC 404 which can cool the image sensor 402 to maintain the image sensor 402 within an operating range. The TEC can draw thermal 426 from the image sensor 402 toward a heat sink 406. The heat sink 406 can disperse the thermal energy 426 or re-route the thermal energy 426 to another element of the image sensor system 400. The image sensor 402 can further include an image sensor cover 408, where the image sensor 402 is positioned to receive light along the optical path 403.

In embodiments as shown in FIG. 4G, a doubled concave sensor window 430 is positioned along the optical path 403 between the image sensor 402 and the sample region 401, where the doubled concave sensor window 430 in part protects the image sensor 402 from foreign elements such as particulate matter or condensation. The doubled concave sensor window 430 can be constructed from a first concave sensor window 432 and a second concave sensor window 434. The first concave sensor window 432 and second concave sensor window 434 can be stacked in combination in front of the image sensor 402 and image sensor cover 408 such that the optical path 403 incident from the sample region passes through the first concave sensor window 432, a first window cavity 433 defined by the first concave sensor window 432, the second concave sensor window 434, and a second concave window cavity 435 defined by the second concave sensor window 434. The first window cavity 433 can thereby function as a primary insulation cavity, regulating the rate of thermal change directly in front of the image sensor 402 and image sensor cover 408, maintaining an operational temperature in that space. The second window cavity 435 can similarly function as a supplementary insulation cavity, regulating the rate of thermal change directly in front of the first concave sensor window 432, maintaining an operational temperature in that space.

The concavity of both the first concave sensor window 432 and the second concave sensor window 434 faces the image sensor 402 and image sensor cover 408, forming the first window cavity 433 and second window cavity 435, respectively, in front of the image sensor cover 408. The doubled concave sensor window 430 can be attached to the image sensor 402 with an adhesive element 410, along an edge of the image sensor 402 surrounding the image sensor cover 408. A thin film 414 can be further applied to the surface of the concave sensor window 432 distal from the image sensor 402 and proximate to the sample region 401. In some embodiments, the thin film 414 can conduct electricity or thermal energy such that the thin film 414 can maintain a controlled temperature, further where the thin film 414 controlled temperature can be greater than an ambient or environmental temperature. In other embodiments, the thin film can be an anti-condensation thin film that does not require connection to an electrical or thermal source to prevent condensation from forming on the doubled concave sensor window 430.

In some aspects, each of the first concave sensor window 432 and the second concave sensor window 434 can be made of glass, where each concave sensor window can have an overall thickness of about one to twenty millimeters (1 mm-20 mm), or any increment or gradient of thickness within that range. Similarly, each of the first window cavity 433 and the second window cavity 435 can have a depth, extending into their respective sensor window, of about one to nineteen millimeters (1 mm-19 mm), or any increment or gradient of thickness within that range. In particular aspects, each of the first concave sensor window 432 and the second concave sensor window 434 can have an overall thickness of about five millimeters (5 mm). In other particular aspects, each of the first window cavity 433 and the second window cavity 435 can have a depth, extending into their respective sensor window, of about one to four millimeters (1 mm-4 mm). Each window cavity can have a width, extending across the center of their respective sensor window that is from about 10% to 90% the width of the overall sensor window. A glass used for either or both of the first concave sensor window 432 and the second concave sensor window 434 can be a standard glass, or can be a glass doped with an element, such as boron (B) making a borosilicate glass, which can modify the index of refraction (IR) or other transmissive characteristics of the first concave sensor window 432 and/or the second concave sensor window 434. In other aspects, either or both of the first concave sensor window 432 and the second concave sensor window 434 can be made of an optically transmissive polymer or plastic, where the polymer or plastic has a coefficient of thermal expansion similar to glass, or a coefficient of thermal expansion similar to the coefficient of thermal expansion for the image sensor 402. In further aspects, either or both of the first concave sensor window 432 and the second concave sensor window 434 can be made of a Pyrex glass, poly (methyl methacrylate) (PMMA or acrylic glass), polycarbonate, poly(vinyl chloride) (PVC), or polytetrafluoroethylene (PTFE). In such embodiments, the first concave sensor window 432 and the second concave sensor window 434 should be selected to have matching or similar indices of refraction ($I_R$). In some aspects, the side of first concave sensor window 432 distal from the image sensor 402 and proximate to the sample region 401 can be generally planar. In some aspects, the side of second concave sensor window 434 distal from the image sensor 402 and proximate to the sample region 401 can be generally planar. In other embodiments, either of both of the first concave sensor window 432 and the second concave sensor window 434 can be a curved concave sensor window or a bulged concave sensor window.

In embodiments where heated, the doubled concave sensor window 430 can both conduct heat and expand due to the heat. Accordingly, materials selected to construct the doubled concave sensor window 430 can be selected to have or be within a range for, either or both of, a particular thermal conductivity (κ) and linear coefficient of thermal expansion ($\alpha_L$). The materials used for the doubled concave sensor window 430 (which for this embodiment, by extension, refers to the materials used for both of the first concave sensor window 432 and the second concave sensor window 434) can be selected based on the size of the overall imaging apparatus, the projected operating ranges of temperature and light intensity of the imaging apparatus, or other design considerations. The thermal conductivity (κ) of the doubled concave sensor window 430 can be used to determine how much heat is needed to provide to the thin film 414 in order to maintain an operating temperature above the ambient environmental temperature for the heated image sensor system 400. The linear coefficient of thermal expansion ($\alpha_L$) of the doubled concave sensor window 430 can be used to determine the dimensions of the sensor window, and can be further selected to expand at a similar rate as the image sensor 402 to ensure the two elements remain coupled via the adhesive element 410. Materials and characteristics of such materials that can be used to form the doubled concave sensor window 430 are set forth in Table 1 above. The values and ranges for these material characteristics are instructive but not exclusive, as other materials can also be used to construct the doubled concave sensor window 430 In some aspects, the doubled concave sensor window 430 can have a thermal conductivity (κ) of about 0.04-1.14 W/(m*K). In other aspects, the doubled concave sensor window 430 can have a linear coefficient of thermal expansion ($\alpha_L$) of about $3 \times 10^{-6}$-$80 \times 10^{-6}$ (1/K).

In further embodiments, the surface of the concave sensor window 412 (or the curved concave sensor window 412', bulged concave sensor window 412", or doubled concave sensor window 430) can have a rough or textured surface which can allow light to pass through along the optical path 403 without adversely distorting the optical path 403, while providing additional structural advantages to the concave sensor window 412. The rough or textured surface of the concave sensor window 412 increases the overall surface area of the concave sensor window 412, thereby allowing for a larger surface area through which heat can be conducted, and thereby prevent formation of condensation on the concave sensor window 412 surface. In yet further embodiments, the rough surface of the concave sensor window 412 can be a zwitter-textured surface, having a nanostructure such that water can deposit and be absorbed on the zwitter-textured surface from the surrounding environment, while simultaneously keeping water droplets generally separated from each other on the zwitter-textured surface such that condensation which would otherwise obscure the optical path 403 does not form on that surface.

In alternative embodiments, a stacked series of concave sensor windows can be tripled concave sensor window, a quadrupled concave sensor window, a quintupled concave sensor window, or the like. The overall thickness of a single sensor window, a single concave sensor window, a stacked series of concave sensor windows, or any combination thereof can in part determine the operating length of the optical path 403, which can be referred to as a Z-length. The Z-length is dependent on the $I_R$ of the one or more sensor windows and how the optical path 403 refracts within the window cavities, as well as the thickness of the sensor windows and length of the window cavities.

Materials that can be used to form transparent thin film dielectrics as discussed herein can include, but are not limited to: indium-tin oxide (ITO), silicon oxides, titanium oxides, tin oxides, zinc oxides, aluminum-zinc oxide (AZO), silicon nitrides, aluminum nitrides, aluminum oxides, zirconium oxides, titanium-zirconium oxides, niobium oxides, titanium-niobium oxides, hafnium oxides, manganese oxides, tantalum oxides, chromium oxides, bismuth oxides, gallium-zinc oxides (GZO), as well as mixtures, variations, and combinations thereof. Such materials can be used in a thin film layer system as any or all of heat-conductive thin films, anti-condensation, and anti-reflection thin films.

In some aspects of the present disclosure, the image sensor assembly sets forth a method of preventing the formation of condensation on a sensor window. The sensor window can be heated to maintain a temperature marginally higher than the ambient environment as one approach for preventing the formation of condensation on a sensor window. In such embodiments, the sensor window can be heated with an element of the imaging instrumentation such as a battery, a TEC connected, or an alternative electric or thermal source. In further embodiments, the sensor window can be shaped or curved to have an insulation cavity, where the space defined by the sensor window adjacent or proximate to an image sensor can function to regulate the temperature of the area in front of the image sensor as an approach for preventing the formation of condensation on a sensor window. The sensor window or curved sensor window can further be shaped to have a curve or bulge that can focus an optical path transmitted through the sensor window onto a specific region of an image sensor and/or sensory element. In alternative aspects, one or more sensor windows or curved sensor windows can be stacked in series in front of the image sensor to provide for an increased degree of temperature regulation. In further alternative aspects, a heating frame can maintain a temperature marginally higher than the ambient environment as one approach for preventing the formation of condensation directly on an image sensor or sensory element. In many embodiments, a temperature controller, which can be an operator-controlled microprocessor system, can be used to set a temperature to maintain in the image sensor assembly.

As provided herein, the imaging instrumentation which captures images of samples located in a target region can be electronically coupled with an imaging instrumentation interface. Such an imaging instrumentation system and imaging instrumentation interface, can be electrically coupled to a microprocessor, (or other such non-transitory computer readable mediums) by wires or by wireless means, and thereby send imaging data signals to the microprocessor. The coupled microprocessor can collect imaging data from the imaging apparatus and/or imaging instrumentation interface can further relay collected information to other non-transitory computer readable mediums, and/or run calculations on collected data and relay the calculated result to a user-operable and/or user-readable display. The imaging data captured by the imaging apparatus can be evaluated according to computer program instructions controlling the microprocessor (either through hardware or software) to analyze or base calculations on specific wavelengths of light emitted by a sample gel, blot, or membrane, and/or specific wavelengths of light used to illuminate a sample gel, blot, or membrane.

The imaging instrumentation can include a microprocessor can further be a component of a processing device that controls operation of the imaging instrumentation, in particular, the thermal set point of the thin film elements in the disclosed image sensor assembly. The processing device, which for example can be a temperature controller, can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

The above description is illustrative and is not restrictive, and as it will become apparent to those skilled in the art upon review of the disclosure, that the present invention may be embodied in other specific forms without departing from the essential characteristics thereof. For example, any of the aspects described above may be combined into one or several different configurations, each having a subset of aspects. Further, throughout the foregoing description, for the purposes of explanation, numerous specific details were set forth in order to provide a thorough understanding of the invention. It will be apparent, however, to persons skilled in the art that these embodiments may be practiced without some of these specific details. These other embodiments are intended to be included within the spirit and scope of the present invention. Accordingly, the scope of the invention should, therefore, be determined not with reference to the above description, but instead should be determined with reference to the following and pending claims along with their full scope of legal equivalents.

What is claimed is:

1. An image sensor assembly, comprising:
    a cooling structure comprising a thermoelectric cooling element (TEC);
    an image sensor, the image sensor being positioned along an optical path to view a sample region, the image sensor further being coupled to and cooled by the cooling structure;
    a sensor window arranged between the image sensor and the sample region;
    an adhesive element arranged to couple the image sensor and the sensor window along an edge of the image sensor:
    a thin film coating an exterior surface of the sensor window;
    a network of optically transparent and thermally conductive nanowires disposed with a repeating pattern within the thin film coating;
    a set of electrical contacts, the electrical contacts comprising one or more resistive heaters; and
    a power source configured to run electrical current through the set of electrical contacts, wherein the electrical contacts are physically connected to the thin film, thermally connecting the TEC and the sensor window, and wherein the sensor window is heated with either or both of heat generated by the TEC conducted through the electrical contacts and electrical current drawn from the power source.

2. The image sensor assembly according to claim 1, wherein the thin film is an anti-fog coating.

3. The image sensor assembly according to claim 1, wherein the image sensor assembly is configured to image electrophoresis gels, nucleic acids blots, protein blots, bioluminescent assay results, and/or chemiluminescent assay results.

4. The image sensor assembly according to claim 1, wherein the cooling structure further comprises a heat sink.

5. The image sensor assembly according to claim 1, wherein the sensor window has a thermal conductivity ($\kappa$) in the range of 0.04-1.14 W/(m*K).

6. The image sensor assembly according to claim 1, wherein the sensor window has a linear coefficient of thermal expansion ($\alpha_L$) in the range of $3\times10^{-6}$-$80\times10^{-6}$(1/K).

7. The image sensor assembly according to claim 1, wherein the sensor window is has a rough or zwitter-textured surface.

8. The image sensor assembly according to claim 5, wherein the sensor window comprises polycarbonate and has a thermal conductivity ($\kappa$) of 0.19 W/(m*K).

9. The image sensor assembly according to claim 5, wherein the sensor window comprises polyvinylchloride (PVC) and has a thermal conductivity ($\kappa$) of 0.19 W/(m*K).

10. The image sensor assembly according to claim 5, wherein the sensor window comprises polytetrafluoroethylene (PTFE) and has a thermal conductivity ($\kappa$) of 0.25 W/(m*K).

11. The image sensor assembly according to claim 5, wherein the sensor window comprises tempered glass and has a thermal conductivity ($\kappa$) in the range of 1.005-1.05 W/(m*K).

12. The image sensor assembly according to claim 5, wherein the sensor window comprises borosilicate glass and has a thermal conductivity ($\kappa$) of 1.14 W/(m*K).

13. The image sensor assembly according to claim 6, wherein the sensor window comprises polycarbonate and has a linear coefficient of thermal expansion ($\alpha_L$) in the range of $37.5\times10^{-6}$-$37.65\times10^{-6}$(1/K).

14. The image sensor assembly according to claim 6, wherein the sensor window comprises polyvinylchloride (PVC) and has a linear coefficient of thermal expansion ($\alpha_L$) of $70\times10^{-6}$(1/K).

15. The image sensor assembly according to claim 1, wherein the sensor window comprises polytetrafluoroethylene (PTFE) and has a linear coefficient of thermal expansion ($\alpha_L$) in the range of $81\times10^{-6}$-$234\times10^{-6}$(1/K).

16. The image sensor assembly according to claim 1, wherein the resistive heaters further comprise two linear resistive heaters.

17. The image sensor assembly according to claim 1, wherein the network of nanowires are formed of silver.

* * * * *